(12) United States Patent
Brechbiel et al.

(10) Patent No.: US 8,535,639 B2
(45) Date of Patent: Sep. 17, 2013

(54) TRIFUNCTIONAL IMAGING AGENT FOR MONOCLONAL ANTIBODY TUMOR-TARGETED IMAGING

(75) Inventors: Martin W. Brechbiel, Annandale, VA (US); Heng Xu, Rockville, MD (US); Kwamena Baidoo, Reisterstown, MD (US)

(73) Assignee: The United States of America, as represented by the Secretary of the Department of Health and Human Services, Washington, DC (US)

( * ) Notice: Subject to any disclaimer, the term of this patent is extended or adjusted under 35 U.S.C. 154(b) by 618 days.

(21) Appl. No.: 12/667,790

(22) PCT Filed: Jul. 16, 2008

(86) PCT No.: PCT/US2008/070133
§ 371 (c)(1),
(2), (4) Date: Feb. 8, 2010

(87) PCT Pub. No.: WO2009/012288
PCT Pub. Date: Jan. 22, 2009

(65) Prior Publication Data
US 2011/0014120 A1 Jan. 20, 2011

Related U.S. Application Data

(60) Provisional application No. 60/929,913, filed on Jul. 17, 2007.

(51) Int. Cl.
*A61K 51/00* (2006.01)
*A61M 36/14* (2006.01)

(52) U.S. Cl.
CPC .................................... *A61K 51/00* (2013.01)
USPC ........................................ 424/1.11; 424/1.37

(58) Field of Classification Search
None
See application file for complete search history.

(56) References Cited

U.S. PATENT DOCUMENTS

| 4,831,175 A | 5/1989 | Gansow et al. |
| 5,099,069 A | 3/1992 | Gansow et al. |
| 5,124,471 A | 6/1992 | Gansow et al. |
| 5,128,121 A * | 7/1992 | Berg et al. ..................... 424/9.32 |
| 5,246,692 A | 9/1993 | Gansow et al. |
| 5,286,850 A | 2/1994 | Gansoh et al. |
| 5,434,287 A | 7/1995 | Gansow et al. |
| 6,335,429 B1 * | 1/2002 | Cai et al. ....................... 530/402 |
| 6,765,104 B1 | 7/2004 | Brechbiel et al. |
| 6,995,247 B2 | 2/2006 | Brechbiel et al. |
| 7,081,452 B2 | 7/2006 | Brechbiel et al. |
| 7,163,935 B2 | 1/2007 | Brechbiel et al. |
| 2004/0192769 A1 * | 9/2004 | Greenwald et al. ........... 514/483 |
| 2005/0147555 A1 | 7/2005 | Fan et al. |
| 2006/0120959 A1 * | 6/2006 | De Haen et al. ............. 424/1.49 |
| 2006/0165600 A1 | 7/2006 | Brechbiel et al. |

FOREIGN PATENT DOCUMENTS

| EP | 1 815 870 A1 | 8/2007 |
| WO | WO 03/014158 A1 | 2/2003 |
| WO | WO 2005/051424 A1 | 6/2005 |
| WO | WO 2007/134236 A2 | 11/2007 |

OTHER PUBLICATIONS

Achilefu et al. *J. Med. Chem.*, 45, 2003-2015 (2002).
Anderson et al., *Nano Ltrs.*, 6(6), 1160-1164 (2006).
Blend et al., *Cancer Biother. Radiopharm.*, 18(3), 355-363 (2003).
Clifford et al., *J. Med Chem.*, 49, 4297-4304 (2006).
Dirksen et al., *Organic Ltrs.*, 6(26), 4857-4860 (2004).
Edwards et al. *Bioconjugate Chem.*, 19, 192-200 (2008).
Frullano et al., *Inorganic Chem.: Commun.*, 45(21), 8489-8491 (2006).
Graham et al. *J. Pharm. Pharmaceut. Sci.*, 10(2), 286s-297s (2007).
Hnatowich et al., *Science*, 220, 613-615 (1983).
Hüber et al., *Bioconjugate Chem.*, 9, 242-249 (1998).
Kobayashi et al., *Clin. Cancer Res.*, 10, 7712-7720 (2004).
Krejcarek et al., *Biochem. Biophys. Res. Commun.*, 77(2), 581-585 (1977).
Manning et al., *Bioconjugate Chem.*, 15(6), 1488-1495 (2004).
Manning et al., *Organic Ltrs.*, 4(7), 1075-1078 (2002).
Milenic et al., *Clin. Cancer Res.*, 10, 7834-7841 (2004).
Milenic et al., *Nature Rev. Drug Disc.*, 3, 488-498 (2004).
Talanov et al., *Nano Ltrs.*, 6(7), 1459-1463 (2006).
Wang et al., *Clin. Cancer Res.*, 11(19 Suppl), 7171s-7177s (2005).
Xu et al., *Clin. Cancer Res.*, 5, 3653-3660 (1999).
Xu et al., *J. Med. Chem.*, 50, 4759-4765 (2007).
Zhang et al., *Photochemistry and Photobiology*, 81, 1499-1504 (2005).

* cited by examiner

*Primary Examiner* — Michael G Hartley
*Assistant Examiner* — Melissa Perreira
(74) *Attorney, Agent, or Firm* — Leydig, Voit & Mayer, Ltd.

(57) ABSTRACT

The present invention relates to trifunctional imaging agents that include an antibody for cell targeting, as well as a chelating moiety for sequestering radioisotopes and a fluorescing moiety for imaging. The invention also provides methods using the conjugates for medical diagnostic imaging.

22 Claims, 5 Drawing Sheets

TRIFUNCTIONAL IMAGING AGENT FOR MONOCLONAL ANTIBODY TUMOR-TARGETED IMAGING

CROSS-REFERENCE TO RELATED APPLICATIONS

This patent application claims the benefit of U.S. Provisional Patent Application No. 60/929,913, filed Jul. 17, 2007, which is incorporated by reference.

BACKGROUND OF THE INVENTION

Multimodality imaging is a clinical tool for imaging human diseases, such as cancers (Moseley et al., *Stroke* 2004, 35, 2632-2634). Dual mode labeled imaging agents allow the same target to be evaluated with two different modalities, such as positron emission tomography (PET) and computed tomography (CT) (Blodgett et al., *Radiology,* 2007, 242, 360-85), and magnetic resonance imaging (MRI) and near-infrared spectroscopy (NIR) optical imaging (OI) (Jaffer et al., *JAMA,* 2005, 293, 855-862). The strengths of each imaging mode are thereby combined in a single imaging session, thereby improving diagnostic accuracy. The multimodality imaging approach is widely considered to provide a more precise, multiparametric description of a disease process with information such as location, extent, metabolic activity, blood flow, and function of target tissue. This description enables better characterization of disease processes. However, the development of imaging agents for multimodality imaging is more challenging than development of single mode agents. Design, synthesis, and selection of nuclear and/or optical tracers is complicated by the need to avoid physical-chemical interference between molecular components. Few examples of multimodality agents have been reported in the literature and even fewer have been carried forward for investigation and evaluation in vivo (Hüber et al., *Bioconjugate Chem.,* 1998, 9, 242-249, Dirksen et al., *Org. Lett.,* 2004, 6, 4857-5860, Manning et al., *Org. Lett.,* 2002, 4, 1075-1078, and Talanov et al., *Nano Lett.,* 2006, 6, 1459-1463). For example, Hüber et al. reported imaging agents in which gadolinium$^{3+}$-diethylenetriaminepentaacetic acid (Gd(III)-DTPA) and a rhodamine dye were attached to a polymeric framework. However, the imaging agent did not include functionality intended to target specific diseased cells (Hüber et al., *Bioconjugate Chem.,* 1998, 9, 242-249). Dirksen et al. labeled a cyclic peptide with both Gd(III)-DTPA and Oregon Green 488 to allow for targeted dual mode fluorescence microscopy and magnetic resonance imaging (Dirksen et al., *Org. Lett.,* 2004, 6, 4857-5860). Manning et al. coupled a Gd(III) chelated peripheral-type benzodiazepine receptor ligand to cyclen-based fluorophores to produce an agent that allowed for targeted dual mode fluorescence microscopy and magnetic resonance imaging (Manning et al., *Org. Lett.,* 2002, 4, 1075-1078). However, in current clinical practice multimodality imaging usually utilizes different imaging agents for each modality. For example, in PET/CT, $^{18}$F-deoxyglucose is used for the PET component and iodinated contrast media is used for the CT.

BRIEF SUMMARY OF THE INVENTION

The invention relates to a trifunctional imaging agent, which combines: the targeting property of tumor-specific monoclonal antibodies (mAbs), the high sensitivity afforded by fluorescing moieties, and the capability to image radioisotope probes deep within tissue. Given the trifunctional nature, a single imaging agent possessing the signaling components for multiple imaging modalities can be administered. As a result, the pathology could be more precisely co-localized based on the two or more sets of information provided by the multiple imaging modalities. By providing the signaling agents for each mode on the same targeting vector, differences in the distribution of the signaling agents can be minimized. Accordingly, because of the targeting properties of mAbs and the application of radiolabeled mAb imaging and therapies to cancer diagnosis and treatment, it is envisioned that the imaging agent of the present invention may provide greater efficacy, less toxicity, and greater treatment success than conventional therapies.

In an embodiment, the invention provides a signaling agent of formula (I)

in which Y is a chelating moiety that is complexed to a radioisotope, Z is a fluorescent dye moiety, X is $C_1$-$C_8$ alkyl, cycloalkyl, cycloalkylalkyl, aryl, or aralkyl, and L is $C_1$-$C_8$ alkyl, alkyl ether, or an amino acid residue.

Also provided is an imaging agent comprising an antibody covalently bonded to at least one signaling agent, in which the signaling agent comprises a chelating moiety, a radioisotope complexed with the chelating moiety, and a fluorescent dye moiety covalently bonded to the chelating moiety.

In another embodiment, the invention provides a compound comprising a chelating moiety, a radioisotope complexed with the chelating moiety, and a fluorescent dye moiety such as Cy5.5 or Cy7 covalently bonded to the chelating moiety.

In another embodiment, a composition comprising at least one compound of the invention and a carrier is provided.

A method for diagnostic imaging in a host is further provided. An embodiment of the method comprises administering to the host an imaging agent, in an amount effective to provide an image; and exposing the host to an energy source, whereupon a diagnostic image is obtained.

DETAILED DESCRIPTION OF THE INVENTION

In an embodiment, a signaling agent according to the invention can have formula (I):

(I)

wherein
Y is a chelating moiety that is complexed to a radioisotope,
Z is a fluorescent dye moiety covalently bonded to L,
X is $C_1$-$C_8$ alkyl, cycloalkyl, cycloalkylalkyl, aryl, or aralkyl, and
L is $C_1$-$C_8$ alkyl, alkyl ether, or an amino acid residue.

The signaling agent of formula (I) includes a reactive maleimide group for conjugation to a targeting vector.

In a preferred embodiment, the signaling agent of formula (I) has the structure of formula (Ia), (Ib), (Ic), or (Id):

wherein the definitions of L, X, Y, and Z are the same as for formula (I).

The moiety X is selected from the group consisting of $C_1$-$C_8$ alkyl, cycloalkyl, cycloalkylalkyl, aryl, or aralkyl. The $C_1$-$C_8$ alkyl for X is an alkylene moiety of the structure —$(CH_2)_n$—, where n is 1-8. The $C_1$-$C_8$ alkyl can include branched moieties.

The cycloalkyl group means a cyclic moiety containing from, for example, 1-3 rings (i.e., monocyclic, bicyclic, tricyclic, or spiro), 3 to 8 carbon atoms per ring, preferably from 5 to 8 carbon atoms, more preferably from 5 to 6 carbon atoms. Examples of such moieties include cyclopropyl, cyclobutyl, cyclopentyl, cyclohexyl, and the like. Preferably, the cycloalkyl is cyclopentyl or cyclohexyl. A cycloalkylalkyl group means a cycloalkyl group as described herein connected to an alkylene moiety. An example of a cycloalkylalkyl group is cyclohexylmethyl or cyclohexylethyl. When X is a cycloalkyl or cycloalkylalkyl, the connectivity between the maleimide group and the amido group is at any suitable position on the ring (e.g., at the 1,2, 1,3, or 1,4 positions).

The aryl group refers to an unsubstituted or substituted aromatic carbocyclic moiety, as commonly understood in the art, and includes monocyclic and polycyclic aromatics such as, for example, phenyl, biphenyl, naphthyl, anthracenyl, pyrenyl, and the like. An aryl moiety generally contains from, for example, 6 to 30 carbon atoms, preferably from 6 to 18 carbon atoms, more preferably from 6 to 14 carbon atoms and most preferably from 6 to 10 carbon atoms. It is understood that the term aryl includes carbocyclic moieties that are planar and comprise 4n+2 π electrons, according to Hückel's Rule, wherein n=1, 2, or 3. Preferably, the aryl is phenyl. An aralkyl group means an aryl group as described herein connected to an alkylene moiety. An example of an aralkyl group is benzyl, phenethyl, or phenpropyl. When X is an aryl or aralkyl, the connectivity between the maleimide group and the amido group is at any suitable position on the ring (e.g., at the 1,2, 1,3, or 1,4 positions). Preferably the connectivity is at the 1,3 or 1,4 positions.

In a preferred embodiment, X is selected from the group consisting of $C_2$-$C_5$ alkyl (—$(CH_2)_{2-5}$—), cyclohexyl-$C_1$-$C_4$ alkyl (—$C_6H_8$—$(CH_2)_{1-4}$—), phenyl (—$C_6H_4$—), and phenyl-$C_1$-$C_4$ alkyl (—$C_6H_4$—$(CH_2)_{1-4}$—).

L is selected from the group consisting of $C_1$-$C_8$ alkyl, alkyl ether, and an amino acid residue. The $C_1$-$C_8$ alkyl for L is an alkylene moiety of the structure —$(CH_2)_n$—, where n is 1-8. The $C_1$-$C_8$ alkyl can include branched moieties. The alkyl ether has the structure —$(CH_2)_{1-8}$—O—, Preferably, L is $C_1$-$C_8$ alkyl, and more preferably L is $C_2$-$C_5$ alkyl. Most preferably L is $C_4$ alkyl.

The amino acid residue, which can be natural or synthetic, is preferably one of the twenty naturally occurring amino acids (e.g., methionine, threonine, cysteine, serine, alanine, valine, leucine, isoleucine, phenylalanine, tyrosine, histidine, tryptophane, aspartic acid, asparagine, glutamic acid, glutamine, lysine, arginine, glycine, and proline). More preferably, L is glycine, alanine, valine, or lysine. When L is an amino acid residue, the acidic and amino functional groups are part of the core structure depicted in the structure of formulae (I), (Ia), (Ib), (Ic), and (Id).

A chelating agent or moiety can refer to a chemical compound or a part of a chemical compound that can form a ring or a portion of a ring in the proximity of a metal atom. In the proximity of the metal atom, the chelating agent or moiety can form one or more coordinate bonds with the metal atom. Typically the multidentate ligand is selected based on the coordination chemistry of the chosen radionuclide. For example, the multidentate ligand can be based on diethylenetriaminepentaacetic acid ("DTPA"), 1,4,7-triazacyclononane-N,N',N''-triacetic acid ("NOTA"), or 1,4,7,10-tetraazacyclododecane-N,N',N,'',N'''-tetraacetic acid ("DOTA").

The chelating moiety (Y) can be, for example, CHX-A" (N—[(R)-2-amino-3-(p-aminophenyl)propyl]-trans-(S,S)-cyclohexane-1,2-diamine-N,N,N',N,"N"-pentaacetic acid), 1B4M (2-(4-aminobenzyl)-6-methyl-diethylenetriamine-pentaacetic acid)), 1B4M-DTPA (2-(p-aminobenzyl)-6-methyl-1,4,7-triaminoheptane-N,N',N"-pentaacetic acid), C-DOTA (2-(p-aminobenzyl)-1,4,7,10-tetraazacyclododecane-N,N',N,"N'"-tetraacetic acid), PA-DOTA (1,4,7,10-tetraaza-N-(1-carboxy-3-(4-nitrophenyl)propyl)-N',N",N'"-tris (acetic acid)cyclododecane), or TCMC (2-(p-aminobenzyl)-1,4,7,10-tetraazacyclododecane-N,N'N,"N'"-tetracarboxamide).

Other suitable DOTA derivatives include those that that are backbone-substituted. For example, the multidentate ligand can be a compound of formula (I), (II), or (III):

wherein R is hydrogen or alkyl and R' is selected from the group consisting of hydrogen, halo, alkyl, hydroxy, nitro, amino, alkylamino, thiocyano, isothiocyano, carboxyl, carboxyalkyl, carboxyalkyloxy, amido, alkylamido, and haloalkylamido.

Additional examples of suitable chelating moieties (Y) are described in, for example, U.S. Pat. Nos. 7,163,935, 7,081,452, 6,995,247, 6,765,104, 5,434,287, 5,286,850, 5,246,692, 5,124,471, 5,099,069, and 4,831,175 and U.S. Patent Application Publication No. 2006/0165600.

Coupling of a chelating moiety to the fluorescent dye moiety and/or core structure of the signaling agent can be accomplished by several known methods (see, for example, Krejcarek et al., *Biochem. Biophys. Res. Commun.*, 30, 581 (1977); and Hnatowich et al., *Science*, 220, 613 (1983)). For example, a reactive moiety present in a backbone or sidechain substituent (e.g., amino, isothiocyano) is coupled with a second reactive group located on the fluorescent dye moiety and/or core structure of the signaling agent. Typically, a nucleophilic group is reacted with an electrophilic group to form a covalent bond between the chelating moiety and the fluorescent dye moiety and/or core structure of the signaling agent.

Preferably, the backbone or side chain substituent on the chelating moiety is a substituent that conjugates the chelating moiety to the fluorescent dye moiety and/or core structure of the signaling agent. This substituent is desirably a free-end amino group or nitro group, which can be reduced to an amino. An amino group can be covalently bonded to the carboxylate end of an amino acid or amino acid derivative. If necessary, the amino group can be activated with a compound, such as thionyl chloride, to form a reactive chemical group, such as an isothiocyanate. An isothiocyanate is useful because it links directly to an amino residue of an amino acid or amino acid derivative. The aniline group can be linked to an oxidized carbohydrate on the protein and, subsequently, the linkage fixed by reduction with cyanoborohydride. The amino group also can be reacted with bromoacetyl chloride or iodoacetyl chloride to form —NHCOCH$_2$Z, with Z being bromide or iodide. This group reacts with any available amine or sulfhydryl group on a biomolecule to form a stable covalent bond. The most desirable backbone or sidechain substituents for multidentate ligands are members selected from the group consisting of hydrogen, halo, alkyl, hydroxy, nitro, amino, alkylamino, thiocyano, isothiocyano, carboxyl, carboxyalkyl, carboxyalkyloxy, amido, alkylamido and haloalkylamido. In some preferred instances, the backbone or sidechain substituent is an amino group, a haloalkylamido of the formula —NHCOCH$_2$Z, with Z being bromide or iodide, or isothiocyano (—NCS).

In a preferred embodiment, the chelating moiety (Y) has an amino group that is part of the core structure depicted in the structure of formula (Ia) or (Id).

Radioisotopes of any suitable metal ion are acceptable for forming metal complexes with the chelating moiety. For example, typical radioisotopes include technetium, bismuth, lead, actinium, nitrogen, iodine, fluorine, tellurium, helium, indium, gallium, copper, rhenium, yttrium, samarium, zirconium, iodine, and holmium. Of these radioisotopes, indium is preferred. Specific examples of radionuclides suitable for complexing to a chelating moiety for various imaging techniques, including single photon emission computed spectroscopy, are, for example, $^{18}$F, $^{213}$Bi, $^{212}$Bi, $^{212}$Pb, $^{203}$Pb, $^{225}$Ac, $^{177}$Lu, $^{99m}$Tc, $^{111}$In, $^{124}$I, $^{123}$I, $^{186}$Re, $^{201}$Tl, $^{3}$He, $^{166}$Ho, $^{86}$Y, $^{64}$Cu, $^{89}$Zr, $^{66}$Ga, $^{68}$Ga, and $^{67}$Ga. The radioisotopes $^{64}$Cu, $^{86}$Y, $^{89}$Zr, $^{111}$In, and $^{203}$Pb are especially preferred.

In a preferred embodiment, the metal is a gamma-emitting radioisotope. The gamma-emitting radioisotope can be, for example, a radioactive lanthanide. Specific radioisotopes that are preferred include $^{86}$Y, $^{64}$Cu, 89Zr, $^{124}$I, $^{66}$Ga, $^{68}$Ga, $^{67}$Ga, $^{123}$I, $^{203}$Pb, and $^{111}$In.

To prepare metal complexes of the invention, the chelating moiety is complexed with an appropriate metal or metal ion. This can be accomplished by any methodology known in the art. For example, the metal can be added to water in the form of an oxide, halide, nitrate or acetate (e.g., yttrium acetate, bismuth iodide) and treated with an equimolar amount of chelating moiety. The chelating moiety can be added as an aqueous solution or suspension. Dilute acid or base can be added (where appropriate) to maintain a suitable pH. Heating at temperatures as high as 100° C. for periods of up to 24 hours or more can be employed to facilitate complexation, depending on the metal, the chelating moiety, and their concentrations.

A fluorescent dye, compound, or moiety can emit light of a characteristic wavelength when exposed to light having a wavelength shorter than the characteristic wavelength. The fluorescent dye moiety (Z) can be, for example, an Alexa Fluor dye, e.g., Alexa Fluor 350, 405, 430, 488, 500, 514, 532, 546, 555, 568, 594, 610, 633, 635, 647, 660, 680, 700, or 750 (Invitrogen, Carlsbad, Calif.), a cyanine dye, rhodamine, coumarin, pyrene, dansyl, fluorescein, fluorescein isothiocyanate, carboxyfluorescein diacetate succinimidyl ester, an isomer of fluorescein, R-phycoerythrin, tris(2',2-bipyridyl) dichlororuthenium(II) hexahydrate, Fam, VIC®, NED™, ROX™, calcein acetoxymethylester, $DiIC_{12}$, or anthranoyl.

In a preferred embodiment, the fluorescent dye moiety (Z) is a cyanine dye, e.g., Cy5.5, Cy5, or Cy7 (GE Healthcare, Piscataway, N.J.). More preferably, the fluorescent dye moiety (Z) is Cy5.5:

Cy5.5

Cy5.5 has excitation and emission peaks at 675 nm and 694 nm, respectively. It is a highly sensitive and bright dye with high extinction coefficients and favorable quantum yields. It has superior photostability compared to more commonly used dyes allowing more time for image detection. Cy5.5 is a good candidate for physiological use because it is stable in the pH range of 3 to 10, soluble in aqueous and organic solvents, and has low non-specific binding.

Cy5.5 is commercially available with an N-hydroxysuccinimide (NHS) ester group for binding to amino groups. Thus, a linker comprising a free amino group (e.g., an amino acid or amino acid derivative) can be used to conjugate Cy5.5 to the chelating moiety.

In a preferred embodiment, the fluorescent dye moiety (Z) has a carboxy group for coupling to the core structure of the signaling agent. In this instance, the carbonyl of the carboxy group on Z is part of the core structure depicted in the structure of formula (Ic) or (Id).

An imaging agent of the invention comprises a signaling agent and a targeting vector conjugated to a reactive maleimide group on the signaling agent. In this text, the terms "targeting vector," "biomolecule targeting vector," and "targeting agent" are used interchangeably. A targeting vector can bind to a cell surface antigen associated with malignant disease such as cancer. The targeting vector can be a monoclonal antibody or a monoclonal antibody fragment (e.g., peptide) that targets a cell surface antigen or receptor. The cell surface antigen or receptor can be, e.g., HER2, HER1, egr-1, Muc-1, Muc-4, somatostatin receptor, α-MSH, GRP, placental alkaline phosphatase, pan carcinoma, polymorphic epithelial mucin, prostate-specific membrane antigen, α-fetoprotein, B-lymphocyte surface antigen, truncated EGFR, idiotypes, gp95/gp97, N-CAM, cluster w4, cluster 5A, cluster 6, PLAP, CA-125, ESA, CD19, CD22, CD37, 250 kD proteoglycan, P55, TCR-IgH fusion, blood group A antigen in B or O type individual, c-erbB-2, erbB-2, erbB-3, erbB-4, IL-2, IL-4, IL-6, MSH, transferrin, tumor vasculature integrins, CD11a, CD11b, CD11c, CD18, CD29, CD51, CD61, CD66d, CD66e, CD106, CDw145, or B-human chorionic gonadotropin.

The targeting vector can be, for example, a polyclonal antibody, a monoclonal antibody, an immunologically reactive fragment of an antibody, an engineered immunoprotein, a protein targeting a receptor, a protein targeting a substrate, a protein targeting a regulatory site on DNA or RNA, a peptide, bombesin, gastrin-releasing peptide, RGB peptide, substance P, neuromedin-B, neuromedin-C, somatostatin, octreotide analogues, metenkephalin, a nucleic acid, a nucleic acid targeting a complementary nucleic acid, a steroid, a hormone, estradiol, neurotensin, melanocyte stimulating hormone, follicle analogues stimulating hormone, leutenizing hormone, human growth hormone, a serum protein, a fibrinolytic enzyme, a biological response modifier, interleukin, interferon, erythropoietin, colony-stimulating factor, a glycoprotein, a glycolipid, a carbohydrate, a small molecular weight cell surface receptor agent, a growth factor hormone, epinephrine, an epinephrine derivative, a histamine, a prostaglandin, or a derivative thereof. In a preferred embodiment, the targeting biomolecule is an antibody (e.g., scFv, $F(ab')_2$, and Fab), a peptide, or a protein. For example, the targeting vector can be an antibody that binds with tumor cells. The monoclonal antibody or monoclonal antibody fragment can be related to an antibody such as an antibody or single chain antibody (scAb) to c-erbB-2, C46 Ab, 85A12 Ab, H17E2 Ab, NR-LU-10 Ab, HMFC1 Ab, W14 Ab, RFB4 Ab to B-lymphocyte surface antigen, A33 Ab, TA-99 Ab, trastuzumab (e.g., Herceptin™) and cetuximab (e.g., Erbitux™, ImClone and Bristol-Myers-Squibb). Preferably, the mAb is trastuzumab or cetuximab.

Figure 1A:
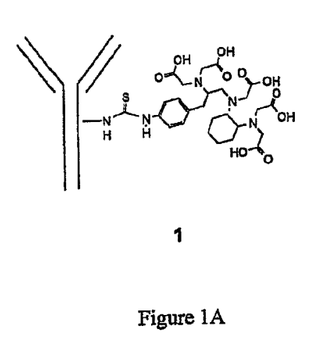
FIG. 1A illustrates the structure of CHX-A"-conjugated trastuzumab (1).

In a particularly preferred embodiment, the targeting vector is trastuzumab. Trastuzumab is a humanized mAb that targets HER2 on epithelial cancer cells. Trastuzumab is commercially available from Genentech as Herceptin™ (San Francisco, Calif.). In an embodiment, a signaling agent can be conjugated to Herceptin™ to form an imaging agent useful for visualizing cancer cells that over-express HER2. For example, the structure of the conjugate 1 of CHX-A" with trastuzumab is illustrated in FIG. 1A (Milenic et al., *Nature Rev. Drug Disc.* 2004, 3, 488-499; Milenic et al., *Clin. Cancer Res.*, 2004, 10, 7834-7841; and Blend et al., *Cancer Biother. Radiopharm.*, 2003, 18, 355-363). An immunoconjugate such as 1 can exhibit efficient tumor targeting, excellent conservation of binding affinity functionality after covalent conjugation, and a normal whole body clearance pattern.

An embodiment of the invention provides a compound that comprises a chelating moiety, a radioisotope complexed with the chelating moiety; and a dye moiety covalently bonded to the chelating moiety. The chelating moiety and dye moiety are as described herein. In preferred embodiments, the chelating moiety is CHX-A", 1B4M, 1B4M-DTPA, C-DOTA, or TCMC, and the dye moiety is Cy5.5 or Cy7.

In some instances, the core structure of the compound can include at least one amino acid or amino acid derivative to which the chelating moiety and dye moiety are covalently bonded. In addition, a biomolecule targeting vector can be covalently bonded to the chelating moiety and the dye moiety of the compound through, for example, through the core structure of the at least one amino acid or amino acid derivative.

The amino acid or amino acid derivative can be a diamino carboxylic acid (i.e., an organic molecule that contains two amino groups and one carboxylic acid group). For example, the amino acid can be lysine or the amino acid derivative can be a lysine derivative. Alternatively, the amino acid derivative can be a maleimide active ester-functionalized amino acid. For example, the maleimide active ester can be N-[γ-maleimidobutyryloxy]succinimide ester, m-maleimidobenzoyl-N-hydrosuccinimide ester, succinimidyl-4-[N-maleimidomethyl]cyclohexane-1-carboxy-[6-amido caproate], succinimidyl-6-[β-maleimidopropionamido]hexanoate, succinimidyl-4-[p-maleimidophenyl]butyrate, N-[ε-maleimidocaproyloxy]-succinimide ester, succinimiidyl-4-[N-maleimidomethyl]cyclohexane-1-carboxylate, N-[(β-maleimidopropyloxy]succinimide ester, N-[α-maleimidoacetoxy]succinimide ester, and m-maleimidoaryl-N-hydrosuccinimide ester (Pierce Chemical). The amino acid derivative can be a maleimidomethyl cyclohexane carboxylate functionalized lysine.

In another embodiment, a signaling agent can be synthesized by (a) condensing a diamino acid derivative with a chelating moiety (Y), (b) selectively reacting one amino group of the diamino acid derivative with a fluorescent dye moiety (Z) to form a covalent bond, and (c) selectively reacting a second amino group on the diamino acid derivative with a moiety to introduce a maleimide group with a linker (X) to form a covalent bond.

To introduce a maleimide group into the signaling agent, a bifunctional linker can be used (e.g., a heterobifunctional linker or a homobifunctional linker). Suitable maleimide-containing bifunctional linkers include sulfosuccinimidyl 4-(N-maleimidomethyl)cyclohexane-1-carboxylate (SMCC), succinimidyl-4-[N-maleimidomethyl]cyclohexane-1-carboxyl-[6-amidocaproate] (LC-SMCC), succinimidyl-6-[β-maleimidopropionamido]hexanoate (SMPH), succinimidyl 4-maleimidobutyrate (GMBS), N-[g-maleimidobutyryloxy]sulfosuccinimide ester (sulfo-GMBS), succinimidyl 6-maleimidocaproate (EMCS), N-[e-maleimidocaproyloxy]sulfosuccinimide ester (sulfo-EMCS), succinimidyl-4-(p-maleimidophenyl)butyrate (SMPB), sulfosuccinimidyl 4-[p-maleimidophenyl]butyrate (sulfo-SMPB), m-maleimidobenzoyl-N-hydroxysulfosuccinimide ester (MBS), m-maleimidobenzoyl-N-hydroxysulfosuccinimide ester (sulfo-MBS), N-k-maleimidoundecanoic acid (KMUA), and N-e-maleimidocaproic acid (EMCA). Other bifunctional linkers are known in the art and are commercially available from, e.g., Pierce Chemical Co. (Rockford, Ill.).

Preferably, the bifunctional linker is SMCC, which is a water-soluble and non-cleavable crosslinker that contains an amine-reactive NHS ester and a sulfhydryl-reactive maleimide group. Amines on an antibody (Ab) or protein form strong amide bonds with the NHS ester of SMCC (Wolcott et al., *Journal of Physical Chemistry B*, 2006, 110, 5779-5789.

To form an imaging agent, a targeting vector can be conjugated to the signaling agent that binds to a cell surface antigen. In a preferred embodiment, a thiol moiety can be introduced into the targeting vector, an extant disulfide in the targeting vector can be reduced to a thiol, or a resident thiol in the targeting vector can be used. For example, a targeting vector (e.g., antibody) can be treated with Traut's reagent to form a free thiol group (Traut et al., *Biochemistry*, 1973, 12, 3266-3273). The number of thiols introduced can be determined, for example, using Ellman's reagent (Ellman et al., *Arch. Biochem. Biophys.*, 1959, 82, 70-77). The thiol moiety of the targeting vector can be reacted with the maleimide group of the signaling agent to form a covalent bond between the targeting vector and the signaling agent. If necessary, the conjugation product of the targeting vector and the signaling agent can be reacted with iodoacetamide to cap unreacted thiol groups. The chelating moiety can be complexed with a radioisotope as described herein (e.g., $^{64}$Cu, $^{86}$Y, $^{89}$Zr, $^{111}$In, or $^{203}$Pb).

Figure 1B:
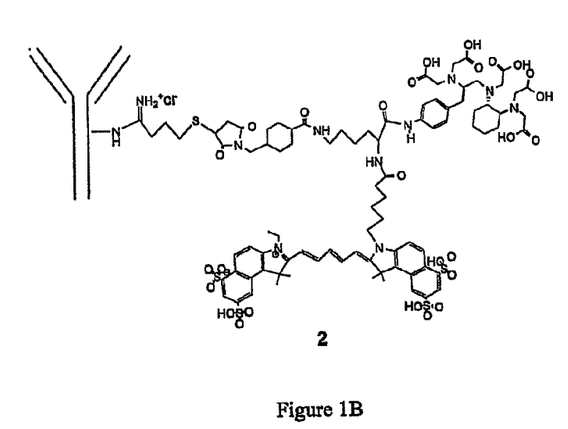
FIG. 1B illustrates the structure of an imaging agent (2), with the dual mode signaling agent, Cy5.5-Lys(SMCC)-CHX-A" (3), conjugated to trastuzumab.

A modular synthetic approach can be used to assemble radioactive metal chelating agents and optical dyes into a single dual-mode (radionuclide-decay imaging and optical imaging) signaling agent for conjugation to antibodies, peptides, or other delivery vectors. For example, a fluorescent dye (e.g., Cy5.5) and a radiometal chelator, e.g., CHX-A" can be directly covalently bonded to the α-NH$_2$ and α-COOH groups of 1-lysine, respectively, while the ε-NH$_2$ group can be used to introduce a maleimide moiety. The chelator can be complexed with a radioisotope, for example, $^{86}$Y for positron emission tomography (PET) imaging, or $^{111}$In for single photon emission computed tomography (SPECT) imaging. The signaling agent (e.g., 3) can be conjugated to a targeting vector of interest, for example, trastuzumab. In a specific example, the imaging agent 2 (FIG. 1B), in which signaling agent 3 is conjugated to a mAb (e.g., trastuzumab), exhibited excellent tumor cell binding comparable with that of the mAb alone.

A signaling agent or compound can refer to a chemical compound or a part of a chemical compound that emits a radiation that can be detected by an instrument. For example, the radiation can be electromagnetic radiation (e.g., one or more photons) or particle radiation. The electromagnetic radiation can have a frequency classified as belonging to any part of the electromagnetic spectrum, including the infrared, visible, ultraviolet, X-ray, and gamma ray regions. The term "light" can, for example, mean infrared, visible, or ultraviolet radiation. The particle radiation can include one or several particles. The particles can be of one or more types of a range of particles, including, for example, positrons, electrons (e.g., beta particles), helium nuclei (e.g., alpha particles), neutrons, elementary particles, agglomerations of elementary particles, fragments of atomic nuclei, whole atomic nuclei, ions, radicals, atoms, or molecules.

In this text, the term "directly covalently bonded" can mean that a covalent bond that may have partial ionic character exists between a first named and a second named chemical species. The term "covalently bonded" can mean that a chain of covalent bonds that may have partial ionic character extends from a first named to a second named chemical species or from a first named to an intermediate unnamed chemical species and from the intermediate unnamed chemical species to a second named chemical species. The term "associated" can mean that any one or more forces associated with chemical phenomena act to maintain a first named chemical species in the proximity of a second named chemical species, including, for example, Van der Waals interactions, hydrophobic interactions, hydrogen bonds, ionic bonds, or covalent bonds. The chemical species can be an atom, ion, radical, molecule, or a biological structure including one or more molecules. The term "preferentially associated" can mean that the energy required to disassociate a first named biological structure, such as an antibody, from a second named biological structure, such as a tumor cell, is greater than the energy required to disassociate a first named biological structure, such as an antibody, from a third named biological structure, such as a normal cell.

The term "near infrared light" can mean radiation in the portion of the electromagnetic spectrum adjacent to that portion associated with visible light, for example, from about 0.7 µm to about 1 µm.

The term "biomolecule" can mean a chemical species associated with a biological organism or with a process of a biological organism. For example, amino acids, peptides, carbohydrates, glycoproteins, glycolipids, nucleic acids, small molecular weight cell surface receptor agents such as hormones, epinephrine, epinephrine derivatives, histamines, and prostaglandins, antibodies, antibody fragments, and immunoglobulins are biomolecules.

An embodiment of the present invention provides a compound including a chelating agent conjugated to a targeting agent. By "targeting agent" is meant any molecule that enables specific interaction with a target. The targeting agent can bind to a defined, target population of cells, for example, through a receptor, a substrate, an antigenic determinant, or another binding site on the target cell population. Cell-surface molecules that are cancer specific antigens (or disease-specific antigens) can serve as targets.

Examples of a targeting agent include an "immunological agent," which is used herein to refer to an antibody, such as a polyclonal antibody or a monoclonal antibody, an immunologically reactive fragment of an antibody, an engineered immunoprotein and the like, a protein (target is receptor, as substrate, or regulatory site on DNA or RNA), a peptide (target is receptor), a nucleic acid (target is complementary nucleic acid), a steroid (target is steroid receptor), and the like. Derivatives and analogs of targeting agents that retain the ability to bind to a defined target can be used. Synthetic targeting agents can be designed, such as to fit a particular epitope. The targeting agent can include any linking group that can be used to join a targeting agent to, for example, a chelate. A variety of linking groups, including bifunctional reagents such as those described herein, can be used.

Examples of cancer-specific, cell-surface molecules include placental alkaline phosphatase (testicular and ovarian cancer), pan carcinoma (small cell lung cancer), polymorphic epithelial mucin (ovarian cancer), prostate-specific membrane antigen, α-fetoprotein, B-lymphocyte surface antigen (B-cell lymphoma), truncated EGFR (gliomas), idiotypes (B-cell lymphoma), gp95/gp97 (melanoma), N-CAM (small cell lung carcinoma), cluster w4 (small cell lung carcinoma), cluster 5A (small cell carcinoma), cluster 6 (small cell lung carcinoma), FLAP (seminomas, ovarian cancer, and non-small cell lung cancer), CA-125 (lung and ovarian cancers), ESA (carcinoma), CD19, 22 or 37 (B-cell lymphoma), 250 kD proteoglycan (melanoma), P55 (breast cancer), TCR-IgH fusion (childhood T-cell leukemia), blood group A antigen in B or O type individual (gastric and colon tumors), and the like.

Examples of cancer-specific, cell-surface receptors include erbB-2, erbB-3, erbB-4, IL-2 (lymphoma and leukemia), IL-4 (lymphoma and leukemia), IL-6 (lymphoma and leukemia), MSH (melanoma), transferrin (gliomas), tumor vasculature integrins, and the like. Examples of cancer specific, cell-surface receptors include erbB-2 and tumor vasculature integrins, such as CD11a, CD11b, CD11c, CD18, CD29, CD51, CD61, CD66d, CD66e, CD106, and CDw145.

The erbB-2 receptor has been found in breast, ovarian, gastric, salivary gland and adeno-carcinomas and in non-small cell carcinomas of the lung. Over-expression of the erbB-2 receptor on such cancers has been found to correlate with poor prognosis. In vitro studies strongly suggest that over-expression of erbB-2 plays an important role in tumor progression.

An example of a single-chain antibody scAb is that which binds c-erbB-2 (WO 93/16185). See, also, WO 93/21232 and H. Zola, *Monoclonal Antibodies*, BIOS Scientific Publishers, Oxfordshire, England (November 1994) for antibody sequences that can be used to construct scAbs.

A number of antibodies to cancer-specific, cell-surface molecules and receptors are known. C46 Ab (Amersham) and 85A12 Ab (Unipath) to carcino-embryonic antigen, H17E2 Ab (ICRF) to placental alkaline phosphatase, NR-LU-10 Ab (NeoRx Corp.) to pan carcinoma, HMFC1 Ab (ICRF) to polymorphic epithelial mucin, W14 Ab to B-human chorionic gonadotropin, RFB4 Ab (Royal Free Hospital) to B-lymphocyte surface antigen, A33 Ab (Genex) to human colon carcinoma, TA-99 Ab (Genex) to human melanoma, antibodies to c-erbB2 (JP 7309780, JP 8176200 and JP 7059588), and the like. ScAbs can be developed, based on such antibodies (see, for example, Bind et al., *Science*, 1988, 242, 423-426, and Whitlow et al., *Methods*, 1991, 2(2), 97-105).

Examples of binding domains include the EOF domain of α-heregulin, α-integrin domain, tumor vasculature peptide motifs. Alpha-heregulin is a ligand with affinity for breast cancer cells expressing the human epidermal growth factor receptors erbB-2, erbB-3 and erbB-4. Heregulin can interact indirectly with erbB-2 via heterodimerization with erbB-3 or erbB-4.

In another embodiment, the invention further provides a composition comprising (a) at least one compound according to an embodiment of the invention (e.g., an imaging agent, a signaling agent); and (b) a carrier. In some embodiments, the carrier can be pharmaceutically acceptable. Pharmaceutically acceptable carriers, for example, vehicles, adjuvants, excipients, and diluents, are well-known to those ordinarily skilled in the art and are readily available to the public. The choice of carrier will be determined, in part, by the particular composition and by the particular method used to administer the composition. Accordingly, there is a wide variety of suitable formulations of the pharmaceutical compositions of the present invention.

A pharmaceutical composition of the invention can be administered to a subject in need of diagnosis and/or treatment, for example a mammal, such as a human patient. The compounds of the invention can be administered in a variety of forms adapted to the chosen route of administration, for example, orally, nasally, intraperitoneally, or parenterally, by intravenous, intramuscular, topical or subcutaneous routes, or by injection into tissue. Thus, compounds of the invention, for example, an imaging agent, can be systemically administered, e.g., by injection, in combination with a pharmaceutically acceptable vehicle such as an inert diluent, orally, in combination with an assimilable edible carrier, or by inhalation or insufflation.

In an embodiment of a composition of the invention, a biologically acceptable, normal saline solution can be appropriately employed. The carrier can include a minor amount of a carrier protein, such as human serum albumin, for example, to stabilize the targeting vector. Stabilizers, antioxidants, osmolality adjusting agents, buffers, pH adjusting agents, etc., can be included in the composition. The composition can be in the form of a solution, suspension, or dispersion. Suitable additives include, for example, physiologically biocompatible buffers, additions of chelants or calcium chelate complexes, or optionally, additions of calcium or sodium salts.

Parenterally administrable forms, e.g., intravenous forms, which are sterile and free from physiologically unacceptable agents and have low osmolality to minimize irritation or other adverse effects upon administration, can be used. Suitable vehicles include aqueous vehicles customarily used for administering parenteral solutions, such as sodium chloride injection, Ringer's injection, lactated Ringer's injection, dextrose injection, dextrose and sodium chloride injection. See, *Remington's Pharmaceutical Sciences,* 15th ed., Easton: Mack Publishing Co. (1975). The solutions can contain preservatives, antimicrobial agents, buffers and antioxidants conventionally used for parenteral solutions, excipients, and other additives that are compatible with chelates and do not interfere with the manufacture, storage or use of products.

An imaging agent or signaling agent can be administered in accordance with the present inventive methods by any suitable route. Such routes include intravenous, intraperitoneal, and the like, depending on the condition, disease, disorder, or cancer to be imaged, the location of the cells of interest, such as diseased, disordered, or cancerous cells, the extent of the condition, disease, disorder, or cancer, and other factors. In the treatment of prostate cancer, for example, transurethral delivery to the prostate or periprostate space or transrectal injection can be used. The requirements for effective pharmaceutical carriers for injectable compositions are well known to those of ordinary skill in the art. See *Pharmaceutics and Pharmacy Practice,* J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

The dose administered to a subject such as a mammal (e.g., a human), in the context of the present invention should be sufficient to affect a therapeutic response in the mammal over a reasonable time frame or an amount sufficient to allow for diagnostic imaging of the desired tissue or organ. The dose will be determined by the strength of the particular compositions employed and the condition of the subject (e.g., human), as well as the body weight of the subject (e.g., human) to be treated. The size of the dose also will be determined by the existence, nature, and extent of any adverse side effects that might accompany the administration of a particular composition. A suitable dosage for internal administration is 0.01 to 100 mg/kg of body weight per day, such as 0.01 to 35 mg/kg of body weight per day or 0.05 to 5 mg/kg of body weight per day. A suitable concentration of the compound in pharmaceutical compositions for topical administration is 0.05 to 15% (by weight), preferably 0.02 to 5%, and more preferably 0.1 to 3%.

The ability to label the same vector with both SPECT- or PET-imaging and optical imaging agents enables both a quantitative gross deep tissue assessment of vector concentration and a micro-cellular distribution of the vector to be obtained by using the same molecule. Products of the dual-mode signaling agent (e.g., 3) are also useful in endoscopy and intraoperative procedures to aid in mapping the borders of tumors during surgery. The chelating chemistry can be selected to adjust for other radioisotopes of interest and any one of a large number of dyes suitable for in vivo imaging can be used. Alternatively, compounds of the invention (e.g., an imaging agent) can be used for in vitro studies. For example, the compounds of the invention can be used in assay studies such as a competition radioimmunoassay or a direct binding radioimmunoassay.

Accordingly, an embodiment of the present invention provides a method for obtaining a diagnostic image in a mammal. In particular, an embodiment of the method comprises administering to the mammal an imaging agent of the invention, in an amount effective to provide an image; and exposing the mammal to an energy source, whereupon a diagnostic image in the mammal is obtained. The diagnostic image can be, for example, single photon emission computed spectroscopy (SPECT) image, positron emission tomography (PET) image, or the like.

Embodiments of the method can be used to image cells, such as cancer cells, in the mammal. One embodiment of the method comprises (a) intravenously administering to a mammal an imaging agent of the invention; (b) contacting a cancer cell surface receptor with the targeting vector of the imaging agent; and (c) observing a fluorescence emission from the fluorescent dye moiety or detecting an emission from the radioisotope by spectroscopy. The spectroscopy can be, for example, SPECT, PET, gamma scintigraphy, or MRI. Preferably, the targeting vector binds to a receptor on the surface of a cancer cell.

The cells are preferably cancer cells, more preferably cancer cells that over-express HER1 and/or HER2. The human epidermal growth factor receptor HER2 (Her2/neu, ErbB2, or c-erb-b2) is a growth factor receptor that is expressed on many cell types. Cancer cells that over-express HER2 are well known in the art and include, for example, epithelial cancers, such as breast, ovarian, pancreatic, and colorectal carcinomas (Milenic et al., *Clinical Cancer Research,* 2004, 10, 7834-7841). Other cancer types known to over-express HER2-proteins include salivary gland cancer, stomach cancer, kidney cancer, prostate cancer, and non-small cell lung cancer. See, for example, Mass (*Int. J. Radiat. Oncol. Biol. Phys.,* 2004, 58(3), 932-940), Wang et al., (*Semin. Oncol.,* 2001, 28(5 Suppl. 16), 115-124), and Scholl et al., (*Ann. Oncol.,* 2001, 12(Suppl. 1), S81-S87). HER1 is epidermal growth factor receptor (EGFR, ErbB1), which is a cell surface glycoprotein. Cancer cells that over-express HER1 also are well known in the art and include, for example, breast cancer, glioblastoma multiforme, lung cancer, head and neck cancer, ovarian cancer, cervical cancer, bladder cancer, and esophageal cancer. See, for example, Nicholson et al. (*Eur. J. Cancer,* 2001, 37(Suppl 4), S9-15).

In a preferred embodiment, Herceptin™ is the target vector in the imaging agent that can target epithelial cancer cells.

For purposes of the present invention, mammals include, but are not limited to, the order Rodentia, such as mice, and the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simioids (monkeys) or of the order Anthropoids (humans and apes). An especially preferred mammal is the human. Furthermore, the host can be the unborn offspring of any of the forgoing hosts, especially mammals (e.g., humans), in which case any screening of the host or cells of the host, or administration of compounds to the host or cells of the host, can be performed in utero.

Through the modular strategy described herein of synthesizing a signaling agent and a conjugate thereof, e.g. a trifunctional imaging agent, potent cytotoxic chemotherapeutic agents, such as geldanamycin or doxorubicin, can be also chemically modified and then attached with either a chelating moiety or a fluorescent dye, generating a single agent for both therapeutic and imaging and tracking purposes.

The following examples further illustrate the invention but, of course, should not be construed as in any way limiting its scope.

EXAMPLES

In the synthetic procedures described herein, experiments with moisture- and/or air-sensitive compounds were carried out under a dried nitrogen or argon atmosphere. For column chromatography, Merck 60 Silica Gel was used (70-230 mesh). Thin-layer chromatography (TLC) was performed on silica gel 60 F-254 plates from EM Reagents. All water used was purified using a Hydro Ultrapure Water Purification system (Rockville, Md.). In the analytical procedures described herein, proton and $^{13}$C NMR data were obtained using a Varian Gemini 300 MHz instrument. Chemical shifts are reported in ppm on the δ scale relative to TMS, TSP, or residual solvent. Proton chemical shifts are annotated as follows: ppm (multiplicity, coupling constant (Hz), integration). Low resolution mass spectra and high resolution mass spectra (HRMS) were obtained on a Waters' LCT Premier time-of-flight mass spectrometer using electrospray ionization (ESI/TOF/MS) in positive ion mode operated at a resolution of 10000. The electrospray capillary voltage was 3 kV and the sample cone voltage was 60 V. Desolvation temperature was 225° C. and the desolvation gas was nitrogen at 300 L/hr. Accurate masses were obtained using the lock spray mode with Leu-Enkephalin as the external reference compound. Cetuximab was obtained from the Veterinary Resources Program Pharmacy at NIH.

Example 1

This example demonstrates a synthesis of boc-Lys(Z)-CHX-A" penta-tert-butyl ester 6 in an embodiment of the invention. See A of FIG. 2.

Figure 2:
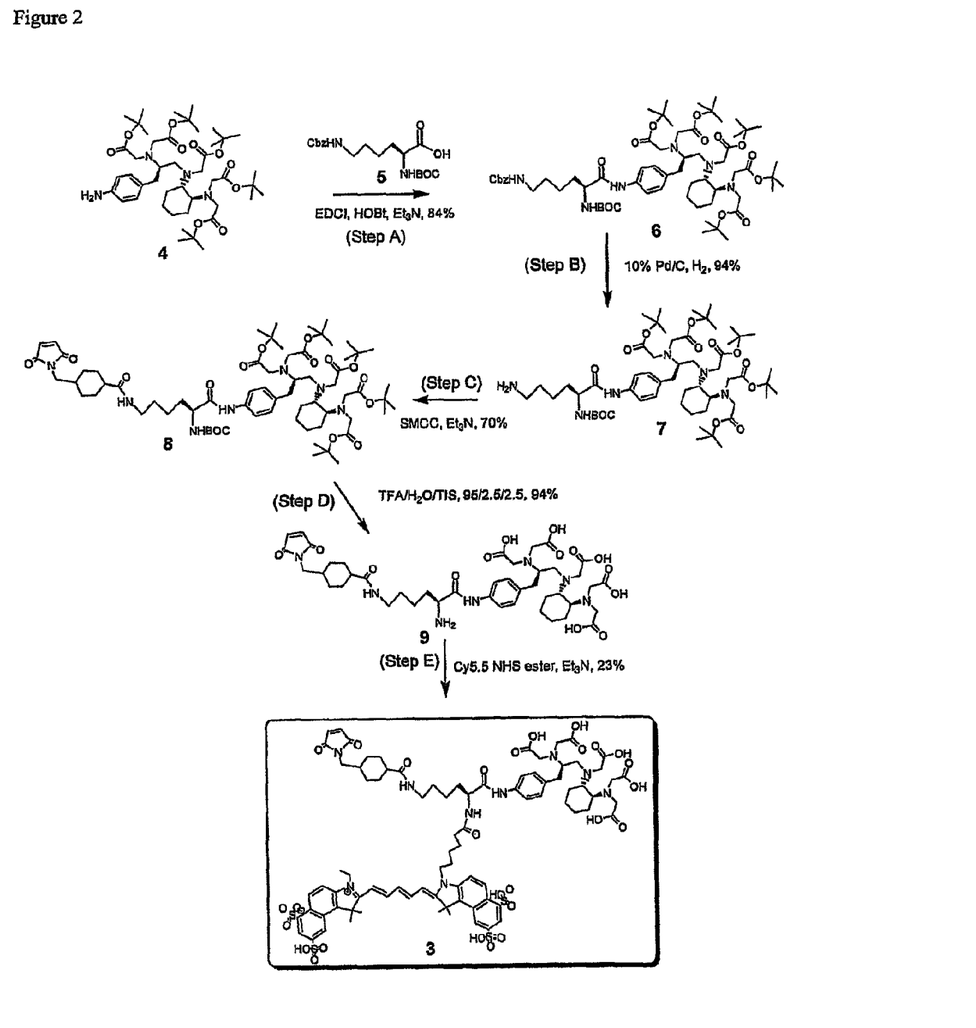
FIG. 2 illustrates a synthetic route in an embodiment of the invention for preparing the dual mode signaling agent Cy5.5-Lys(SMCC)-CHX-A" (3).

Penta-tert-butyl CHX-A" (N[(R)-2-amino-3-(p-aminophenyl)propyl]trans-(S,S)-cyclohexane-1,2-diamine-N,N,N',N,"N"-penta-tert-butylacetate) 4 was prepared by the procedure described in Clifford et al., *J. Med. Chem.* 2006, 49, 4297-4304. First, 0.50 g (1.32 mmol) of lysine derivative Boc-Lys(Z)-OH 5 (Novabiochem, San Diego, Calif.), 0.51 g (2.64 mmol) of 1-ethyl-3-(3-dimethylaminopropyl)carbodiimide (EDCI) (Aldrich/Sigma Chemical Company, St. Louis, Mo.), 0.36 g (2.64 mmol) of 1-hydroxybenzotriazole (HOBt), and triethylamine ($Et_3N$) were added to a stirred solution of 1.00 g (1.20 nmol) of p-amino functionalized penta-tert-butyl CHX-A" 4 in 15 mL of dimethylformamide (DMF). The mixture was left to stir for 24 hours at room temperature (RT) and then concentrated under reduced pressure, diluted with methylene chloride ($CH_2Cl_2$) (100 mL), and washed successively with water (2×100 mL), 5% sodium bicarbonate ($NaHCO_3$) (2×100 mL), and water (1×100 mL). The organic layer was concentrated and the residue was chromatographed on silica gel eluted with ethyl acetate:ethanol (EtOAc:EtOH) (9:1) to afford 1.20 g of the lysine derivative, Boc-Lys(Z)-CHX-A" penta-tert-butyl ester 6, with a yield of 84%.

The following spectroscopic data were obtained. $^1$H NMR (DMSO-$d_6$, 300 Hz) δ 9.77 (s, 1H), 7.45 (d, J=8.7 Hz, 2H), 7.33 (m, 5H), 7.23 (t, J=6.9 Hz, 1H), 7.16 (d, J=8.4 Hz, 2H), 6.92 (d, J=8.1 Hz, 1H), 4.99 (s, 2H), 4.03 (m, 1H), 3.43 (s, 2H), 3.32 (s, 8H), 2.96 (m, 4H), 2.59 (m, 2H), 1.91 (m, 2H), 1.70-1.20 (m, 10H), 1.37 (s, 54H), 1.03 (m, 4H); $^{13}$C NMR: 172.1, 171.9, 171.8, 171.6, 171.5, 170.1, 156.7, 156.2, 137.9, 136.6, 135.4, 130.0, 128.6, 128.2, 119.5, 80.4, 80.3, 80.25, 80.2, 66.7, 64.1, 63.2, 62.7, 54.0, 53.6, 53.1, 52.2, 40.3, 36.2, 31.4, 29.5, 29.3, 28.5, 28.4, 28.1, 27.1, 26.1, 25.9, 22.6. HRMS: calcd for $C_{64}H_{103}N_6O_{15}$ [M+H]$^+$: 1195.7481. Found 1195.7506.

Example 2

This example demonstrates a synthesis of Boc-Lys-CHX-A" penta-tert-butyl ester 7 in an embodiment of the invention. See B of FIG. 2.

The ε-$NH_2$ benzyl carbamate (Cbz) protecting group on the Boc-Lys(Z)-CHX-A" penta-tert-butyl ester 6 was quantitatively cleaved by catalytic hydrogenation as monitored by thin layer chromatography (TLC). A solution of 0.39 g (0.33 mmol) of the Boc-Lys(Z)-CHX-A" penta-tert-butyl ester 6 in 15 mL of methanol (MeOH) was treated with 50 mg of 10% palladium on charcoal catalyst (10% Pd/C) and stirred under a hydrogen atmosphere overnight. The mixture was filtered through Celite 535 (Fluka) and concentrated. The residue was dried under high vacuum to give 0.33 g of amine Boc-Lys-CHX-A" penta-tert-butyl ester 7 at a yield of 94%, which was used without further purification.

The following spectroscopic data were obtained. $^1$H NMR (DMSO-$d_6$) δ 9.81 (s, 1H), 7.45 (d, J=8.4 Hz, 2H), 7.16 (d, J=8.1 Hz, 2H), 6.95 (d, J=7.0 Hz, 1H), 4.12 (m, 1H), 3.44 (s, 2H), 3.33 (s, 8H), 2.96 (m, 2H), 2.80-2.40 (m, 6H), 1.89 (m, 2H), 1.59 (m, 4H), 1.39 (s, 54H), 1.50-1.20 (m, 6H), 1.03 (m, 4H); HRMS: calcd for $C_{56}H_{97}N_6O_{13}$ [M+H]$^+$: 1061.7114. Found 1061.7140.

Example 3

This example demonstrates a synthesis of Boc-Lys(SMCC)-CHX-A"penta-tert-butyl ester 8 in an embodiment of the invention. See C in FIG. 2.

The unprotected ε-$NH_2$ group on the lysine derivative-CHX-A" adduct 7 was reacted with succinimidyl 4-[N-maleimidomethyl]cyclohexane-1-carboxylate (SMCC) (Pierce Biotechnology, Rockford, Ill.). To a solution of 0.33 g (0.31 mmol) of the amine 7 in 10 mL of dimethylformamide (DMF) was added 0.10 g (0.30 mmol) of SMCC and 0.04 mL (0.31 mmol) of triethylamine ($Et_3N$). The mixture was stirred under nitrogen atmosphere at room temperature for 18 hours. Afterwards, the solution was concentrated and the residue was diluted with methylene chloride ($CH_2Cl_2$) (100 mL) and washed successively with water (1×100 mL), 5% sodium chloride ($NaHCO_3$) (1×100 mL), and water (1×100 mL). The organic layer was concentrated and chromatographed on silica gel eluted with ethyl acetate:ethanol (EtOAc:EtOH) (10:0-9:1) to afford 0.27 g of the maleimide, Boc-Lys(SMCC)-CHX-A"-penta-tert-butyl ester 8 as a white solid at a yield of 70%. The maleimide function serves as a highly reactive group towards thiol groups either extant or introduced into proteins or peptides.

The following spectroscopic data were obtained. $^1$H NMR (DMSO-$d_6$, 300 MHz) δ 9.78 (s, 1H), 7.64 (t, J=6.0 Hz, 1H), 7.44 (d, J=7.8 Hz, 2H), 7.16 (d, J=8.4 Hz, 2H), 7.02 (s, 2H), 6.88 (d, J=7.0 Hz, 1H), 4.01 (m, 1H), 3.43 (s, 2H), 3.32 (s, 8H), 3.23 (d, J=6.3 Hz, 2H), 2.97 (m, 4H), 2.59 (m, 4H), 2.01 (m, 2H), 1.80-1.00 (3×m, 22H), 1.37 (s, 54H); HRMS: calcd for $C_{69}H_{112}N_7O_{16}$ [M+H]$^+$: 1280.8009. Found 1280.8040.

Example 4

This example demonstrates a synthesis of $NH_2$-Lys(SMCC)-CHX-A" 9 in an embodiment of the invention. See D of FIG. 2.

Cleavage of the tent-butyl ester on the CHX-A" moiety and the tert-butyl carbamate (BOC) on the α-$NH_2$ group of the lysine function were achieved in one step by treatment of 0.25 g (0.20 mmol) of the maleimide 8 with 10 mL of a solution of 95 vol % trifluoroacetic acid (TFA) (peptide sequence grade, Aldrich/Sigma Chemical Company, St. Louis, Mo.), 2.5 vol % water, and 2.5 vol % triethylsilane (TIS). The reaction mixture was concentrated in vacuum to afford 0.17 g of the carboxyl-functional maleimide (NH$_2$-Lys(SMCC)-CHX-A") 9 in a yield of 94%.

The following spectroscopic data were obtained. $^1$H NMR (DMSO-d$_6$, 300 MHz) δ 10.60 (s, 1H), 7.76 (t, J=6.0 Hz, 1H), 7.63 (d, J=7.8 Hz, 2H), 7.37 (d, J=8.4 Hz, 2H), 7.11 (s, 2H), 4.05 (m, 1H), 3.80-2.60 (m, 20H), 1.80-0.90 (m, 25H), HRMS: calcd for C$_{43}$H$_{62}$N$_7$O$_{14}$ [M+H]$^+$: 900.4355. Found 900.4331.

Example 5

This example demonstrates a synthesis of signaling agent Cy5.5-Lys(SMCC)-CHX-A" 3 in an embodiment of the invention. See E in FIG. 2.

1.0 mg (0.88 μmol) of the mono N-hydroxysuccinimide (NHS) ester of the near infrared dye Cyanine 5.5 (Cy5.5) (GE Healthcare, Piscataway, N.J.) and 20 μL of triethylamine (Et$_3$N) were added to 0.84 mg (0.94 μmol) of the carboxyl-functional maleimide 9 in a solution of 2 mL of dimethylsulfoxide (DMSO) to react the dye with the α-NH$_2$ group on the carboxyl-functional maleimide 9. The reaction mixture was stirred under nitrogen atmosphere at room temperature for 18 hours and then diluted with 20 mL of diethyl ether.

To obtain the signaling agent 3, the precipitated product was purified by reverse-phase high-performance liquid chromatography (RP-HPLC) using a Vydac 5 μm C$_{18}$ reversed-phase 10 mm×25 cm column with a Gilson system equipped with Model 811B solvent mixer and Knauer variable wavelength monitor controlled by Gilson Unipoint System Software. The column was equilibrated with 15 mM ammonium acetate (NH$_4$OAc) (pH 7), and a gradient of acetonitrile (CH$_3$CN) that increased from 0% at 0 min to 50% at 30 min was employed. Lyophilization of the solvent from the relevant fraction was performed to yield 0.36 mg of the signaling agent, the chelate (Cy5.5-Lys(SMCC)-CHX-A") 3 (0.36 mg) with a yield of 22.7%.

The signaling agent 3 was fully characterized by $^1$H NMR, ES-MS, and HPLC. In the $^1$H NMR spectra, the aromatic protons of signaling agent 3 were consistent with those of the published NMR data of Cy5.5 dye, except that there were two additional doublet peaks from the CHX-A" fragment. Negative ion ES-MS of signaling agent 3 gave a m/z ratio of 1797.6 and 897.8 for [M−H]$^-$ and [M−2H]$^{2-}$ respectively; this confirmed the identity of the signaling agent 3. The HPLC spectra of the signaling agent 3 showed a single, symmetric peak, supportive of its high purity. The following spectroscopic data were obtained. $^1$H NMR (DMSO-d$_6$, 300 MHz) δ 8.85 (d, J=9.0 Hz, 2H), 8.80 (s, 2H), 8.36 (m, 2H), 8.25 (d, J=9.0 Hz, 2H), 7.83 (d, J=9.3 Hz, 1H), 7.81 (d, J=9.6 Hz, 1H), 7.43 (d, J=8.1 Hz, 2H), 7.29 (d, J=8.1 Hz, 2H), 6.67 (s, 2H), 4.20 (br triplet, 4H), 3.80-2.60 (m, 22H), 2.34 (t, J=6.0 Hz 2H), 2.15-1.00 (m, 46H); ES-MS m/z: calcd for C$_{84}$H$_{104}$N$_9$O$_{27}$S$_4$ [M+H]$^+$, [M−2H]$^{2-}$: 1798.6, 897.8. Found 1798.3, 897.8.

In an alternative embodiment, in E the free α-NH$_2$ group on the carboxyl-functional maleimide 9 can be functionalized with any one of a large number of dyes in addition to Cy5.5, such as any dye bearing an active ester or isothiocyanate moiety. It can be advantageous to couple the dye to the lysine core in the last part of the synthesis, for example, in step E, because quantum yields of cyanine dyes can be significantly decreased after treatment with strong acids, such as trifluoroacetic acid (TFA).

Example 6

This example demonstrates a radiosynthesis and characterization of Cy5.5-Lys(SMCC)-$^{111}$In-CHX-A" ($^{111}$In-3) in an embodiment of the invention.

A 200-μCi portion of $^{111}$In (Perkin Elmer, Wellesley, Mass.) in 0.05 N HCl was added to signaling agent 3 (Cy5.5-Lys(SMCC)-CHX-A"), dissolved in a solution of 0.15 M ammonium acetate (NH$_4$OAc) having pH 7. The reaction mixture was incubated at 37° C. for 30 min.

An aliquot of the resulting solution was analyzed by RP-HPLC using a Vydac Protein & Peptide C$_{18}$ column equilibrated with 0.015 M ammonium acetate having NH$_4$OAc (pH 7). A 0.0 to 50% gradient of increasing acetonitrile (CH$_3$CN) over 30 min was employed, followed by an additional 10-min plateau at 50% acetonitrile. A UV detector and radiometric detector were coupled to measure absorbance at 254 nm and radioactivity, respectively. Time-resolved elution of the signaling agent 3 (15.0 min) and radiolabeled signaling agent $^{111}$In-3 (16.8 min) was observed following the no-carrier-added complexation reaction, evident from a nearly 2 minute separation between the radiometric and UV peaks, respectively. An analogous carrier-added (with natural indium ($^{nat}$In)) radiolabeling resulted in convergence of the UV peak (16.9 min) and the radiometric peak for $^{111}$In-3 (17.1 min).

Example 7

This example demonstrates a conjugation of signaling agent 3 with trastuzumab to form imaging agent 2 in an embodiment of the invention.

The monoclonal antibody trastuzumab was dialyzed into a thiolation buffer (50 mM NaHCO$_3$, 150 mM NaCl, and 10 mM ethylenediaminetetraacetic acid (EDTA), pH 8.6) and then reacted with 15 molar equivalents of Traut's reagent (2-iminothiolane hydrochloride) (Sigma Chemical Co., St. Louis, Mo.) for 45 minutes at room temperature (Traut et al., *Biochemistry* 1973, 12, 3266-3273). Excess Traut's reagent was removed by passage of the reaction solution through a PD-10 column eluted with the thiolation buffer. The resulting thiol (—SH) groups on trastuzumab were quantified by using Ellman's reagent (5,5'-dithio-bis-2-nitrobenzoic acid) (Ellman et al., *Arch. Biochem. Biophys.* 1959, 82, 70-77, and Riddles et al., *Anal. Biochem.* 1978, 94, 75-81). Based on the molar absorptivity at 412 nm, about 3.5 thiol groups per trastuzumab antibody were found to have been introduced. Just prior to protein conjugation, the signaling agent 3 was dissolved in thiolation buffer and then added drop wise to the solution containing the trastuzumab to achieve a molar reaction ratio of 5 molar equivalents of signaling agent 3 for each of thiolated trastuzumab and gently vortexed. The solution was gently agitated in the dark at room temperature (RT) (25° C.) for 1 hour.

The unreacted thiols were capped with 2.0 mM iodoacetamide solution to minimize cross-linking of antibody product and to achieve a longer shelf life for the immunoconjugate.

The reaction mixture was dialyzed into phosphate-buffered saline (PBS; pH 7.2) at 4° C. with 4 buffer changes over 48 hours to produce the imaging agent, the trastuzumab-Lys (SMCC)-Cy5.5-CHX-A" immunoconjugate 2.

Example 8

This example demonstrates characterization of imaging agent 2 in an embodiment of the invention.

The final protein concentration of the imaging agent, the trastuzumab-Lys(SMCC)-Cy5.5-CHX-A" immunoconjugate 2 was quantified by the Lowry method (Lowry et al., *J. Biol. Chem.* 1951, 193, 265-275) with a bovine serum albumin (BSA) standard. The final protein concentration was found to be 0.901 mg/mL.

In order to assess the final Cy5.5 dye concentration of the immunoconjugate 2, approximately 1.5 mL of the final product was added to a cuvette and the absorbance measured at 675 nm in a Beckman-Coulter DU 520 spectrophotometer (Beckman-Coulter, Inc., Fullerton, Calif., USA). Based on ultraviolet (UV) absorption at 675 nm, the number of Cy5.5 dye moieties per trastuzumab antibody was about 2.4. Given the 1:1 ratio of Cy5.5 and CHX-A" moieties within the signaling agent 3, this corresponds to 2.4 CHX-A" chelate moieties per trastuzumab antibody. Thus, not only does incorporation of Cy5.5 provide a near infrared imaging modality in addition to a PET or SPECT imaging modality, but the incorporation of Cy5.5 also provides a direct readout of the degree of protein modification.

Example 9

This example demonstrates a synthesis of $^{111}$In labeling of imaging agent 2 and of trastuzumab-CHX-A" immunoconjugate 1 in an embodiment of the invention.

Figure 3:
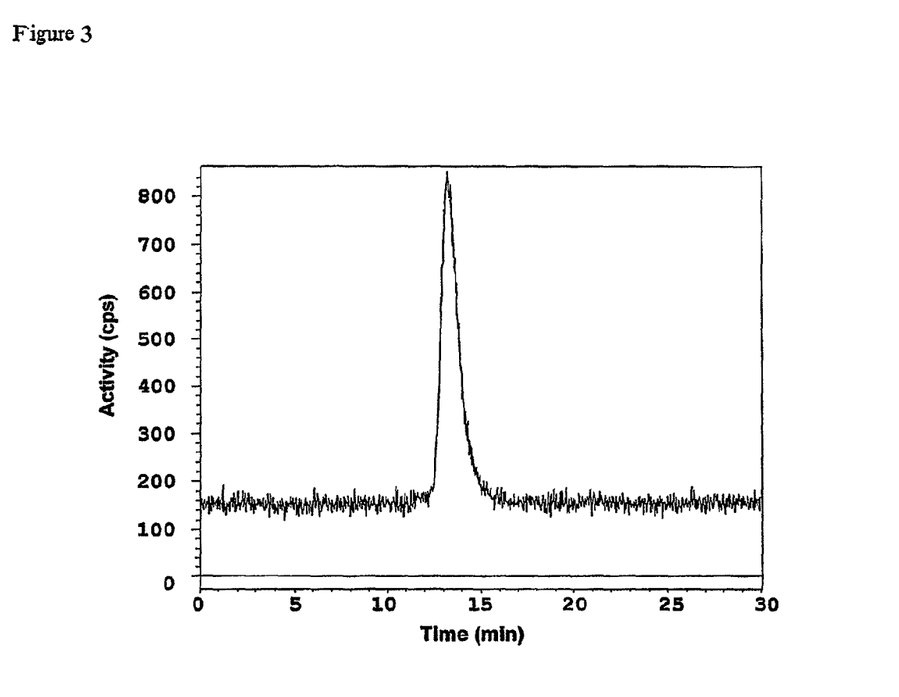
FIG. 3 illustrates an SE-HPLC chromatograph of $^{111}$In-labeled imaging agent $^{111}$In-2 in an embodiment of the invention.

The imaging agent, the trastuzumab-Lys(SMCC)-Cy5.5-CHX-A" immunoconjugate 2 and the trastuzumab-CHX-A" immunoconjugate 1 were each labeled with $^{111}$In (Milenic et al., *Clin. Cancer Res.*, 2004, 10, 7712-7720). The pH of a solution of $^{111}$InCl$_3$ in 0.05 M HCl (0.85 mCi, 2.5 µL) in a vial was adjusted to 4.5-5.0 with aqueous ammonium acetate (NH$_4$OAc) (150 µL, 0.15 M, pH 7.0). Solutions of the respective immunoconjugates in phosphate-buffered saline (PBS) (50 µg, 8-50 µL) were brought up to 100 µL with ammonium acetate (NH$_4$OAc) (0.15 M, pH 7.0) and then added to the $^{111}$In solution, mixed, and incubated at room temperature for 30 minutes. The reaction was quenched by the addition of 10 µL of a 0.001 M solution of diethylenetriaminepentaacetic acid (DTPA) at pH 6.5. Protein bound $^{111}$In was separated from unbound $^{111}$In using a PD-10 column pre-equilibrated and eluted with PBS. The labeling efficiency ranged from 79-96%. FIG. 3 illustrates the size exclusion HPLC profile of the radiolabeled imaging agent, the trastuzumab-Lys (SMCC)-Cy5.5-$^{111}$In-CHX-A" ($^{111}$In-2).

Example 10

This example demonstrates the immunoreactivity of imaging agent 2 in an embodiment of the invention.

The immunoreactivity of imaging agent 2 to SKOV3 cells was found to be retained using three in vitro analytical methods: flow cytometry, competition radioimmunoassay, and direct binding radioimmunoassay. In these methods, the ovarian adenocarcinoma cell line SKOV3 (ATCC, Manassas, Va.) was used. SKOV-3 has been shown to express at least 5×10$^5$ HER2 molecules per cell (Xu et al., *Clin. Cancer Res.* 1999, 5, 3653-3660). The cells were grown in McCoy's 5A medium (Quality Biological Inc., Gaithersburg, Md.) containing 10% Fetalplex (Gemini Bioproducts, Woodland, Calif.) and 1% non-essential amino acids (BioWhittaker, Walkersville, Md.) in a humidified incubator at 37° C. in 5% carbon dioxide (CO$_2$).

Figure 4:
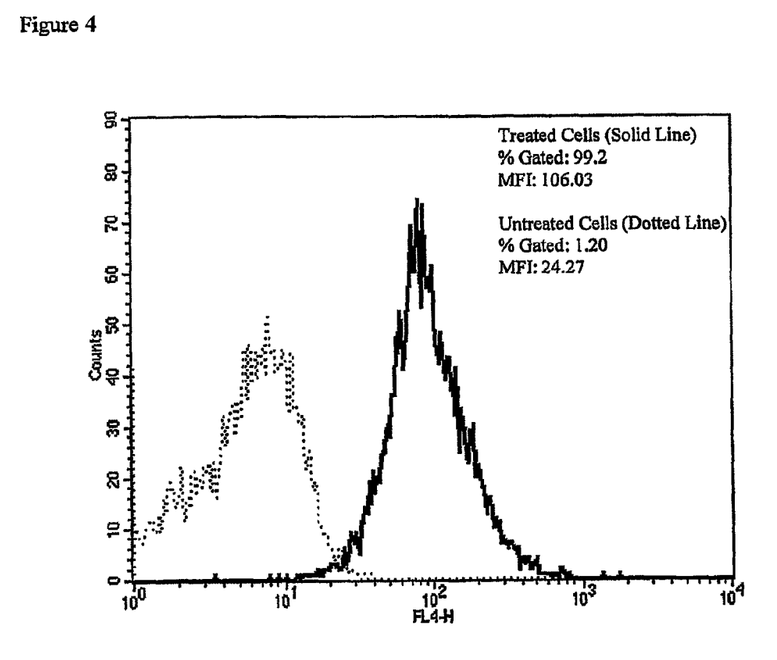
FIG. 4 illustrates the results of evaluation of imaging agent 2 by flow cytometric analysis. Cells incubated with imaging agent 2 (solid line) were 99.2% positive with a mean fluorescence intensity of 106.0 while those in buffer (dotted line) only were 1.2% positive with a mean fluorescence intensity of 24.3.

Flow cytometry: The immunoreactivity of imaging agent 2 was confirmed with HER2 expressing SKOV3 cells using flow cytometric methods. The cells were incubated with 1.25 µg of trastuzumab for 1 hour at 4° C. in PBS containing 1% bovine serum albumin at pH 7.2 (BSA-PBS). Following three washes, the cells were then re-suspended in 1 mL of PBS. The cells (10,000 events collected) were analyzed using a FACS-Calibur flow cytometer with CellQuest software (Becton-Dickinson, Franklin Lakes, N.J.). 99.2% of the cells were positive, expressing the target antigen of trastuzumab and exhibiting fluorescence with a mean fluorescence intensity of 106, as shown by the solid line profile in FIG. 4. By contrast, only 1.2% of the cells in buffer were positive, with a mean fluorescence intensity of 24. Thus, flow cytometry demonstrated the ability of imaging agent 2 to bind the cell surface antigen HER2.

Competition Radioimmunoassay: In preparation for the competition radioimmunoassay, SKOV3 cells were plated on a 96-well plate (about 3×10$^5$ cells/well) and incubated for 6 days. The wells were washed with cold PBS and 200 µL of a cold 80% methanol (MeOH) solution was added to each well. Following an overnight incubation at 4° C., the wells were washed three times with 200 µL of PBS and 200 µL of 1% BSA-PBS was added. After 30 minutes at room temperature (RT), the wells were aspirated and serial dilutions of imaging agent 2 (5000 ng-0.08 ng) were then added to the wells in triplicate (50 µL) followed by the addition of ~33 nCi (50 µL in BSA-PBS) of trastuzumab-$^{111}$In-CHX-A". The radioimmunoassay was incubated overnight at room temperature. On the following day, the wells were washed three times with 200 µL of BSA-PBS. The radioactivity was removed from the wells by adding 100 µL of 0.2 M sodium hydroxide (NaOH) solution, gently shaking the plate for 10 minutes, and adsorbing the solution to filters (Molecular Device Corp., Sunnyvale, Calif.). The filters were placed in 12×75 mm polypropylene tubes and the radioactivity counted in a γ-scintillation counter (WizardOne, PerkinElmer, Shelton, Conn.). The assay included unmodified trastuzumab and HuM195, an anti-CD33 humanized mAb, (a generous gift from D. Scheinberg, Memorial Sloan Kettering Cancer Center) (Nikula et al., *J Nucl. Med.* 1999, 40, 166-176) which served as negative controls. The assay also included wells to which no competitor was added. The percent inhibition was calculated.

Figure 5:
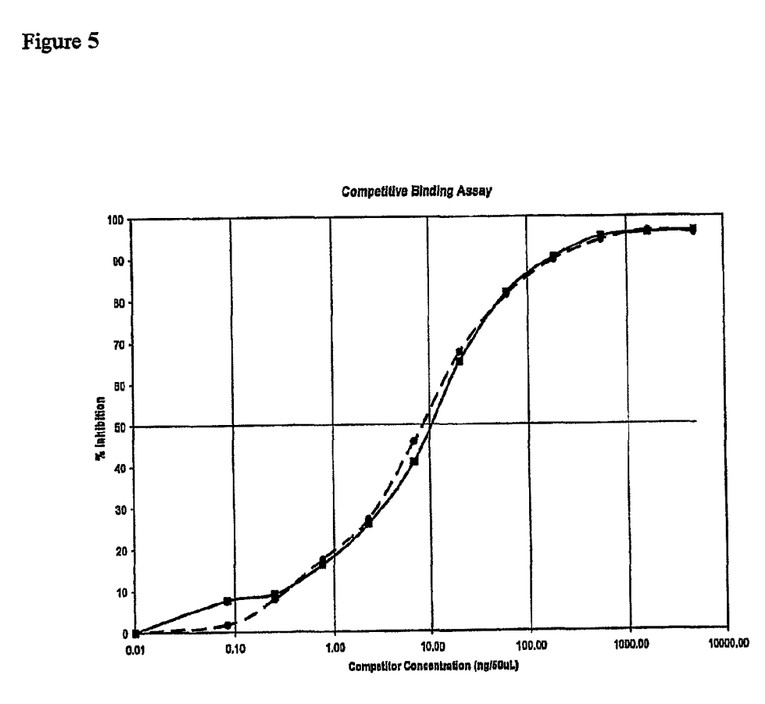
FIG. 5 illustrates the results of a competition radioimmunoassay in which the ability of imaging agent 2 (solid line) (a) to react with HER2-expressing SKOV-3 cells and (b) to displace $^{111}$In-trastuzumab was compared to the ability of unmodified trastuzumab (dashed line) to do the same. The results show that conjugation of trastuzumab with signaling agent 3 to form imaging agent 2 does not alter its native immunoreactivity.

The results of the competition radioimmunoassay are shown in FIG. 5. A comparison of the curves of percent inhibition versus competitor concentration for the imaging agent 2 (solid line) and unmodified trastuzumab (dashed line) demonstrated that modification of trastuzumab with the signaling agent 3 to produce imaging agent 2 did not affect immunoreactivity (see FIG. 5). That is, the 10 ng amount of imaging agent 2 required for 50% inhibition was comparable to the 9 ng amount of native trastuzumab required for 50% inhibition.

Direct Binding Radioimmunoassay: The immunoreactivity of the radiolabeled imaging agent $^{111}$In-2 was assessed in a direct binding radioimmunoassay and compared to radiolabeled trastuzumab modified with just the CHX-A" chelate (trastuzumab-$^{111}$In-CHX-A") $^{111}$In-1. The immunoreactivity of the radiolabeled imaging agent $^{111}$In-2 was assessed using methanol-fixed SKOV3 cells. The cells were trypsinized, pelleted, and re-suspended in 5 mL of PBS. Cold methanol (20 mL) was then added dropwise while vortexing to yield a final solution of 80% methanol. After sitting overnight at 4° C., the cells were washed with PBS, pelleted, re-suspended hi BSA-PBS and aliquoted (2×10$^6$ in 50 µL) into 12×75 mm polypropylene tubes. Serial dilutions (~84 to ~2 nCi) of the radiolabeled imaging agent $^{111}$In-2 or of the radiolabeled trastuzumab-$^{111}$In-CHX-A" (for comparison) were added to the cells in duplicate and gently vortexed. The cells were washed with BSA-PBS following an overnight incubation at room temperature, pelleted, and the radioactivity measured in a γ-scintillation counter (WizardOne). The percent binding was calculated for each dilution and the values presented represent an average of the serial dilutions. In order to confirm the specific reactivity of the radiolabeled imaging agent $^{111}$In-2, additional cells were incubated with about 84 nCi of the radiolabeled imaging agent $^{111}$In-2 along with a 10 µg excess of either unlabeled trastuzumab or unlabeled imaging agent 2.

The results of the direct binding radioimmunoassay were as follows. The percent binding of the radiolabeled imaging agent $^{111}$In-2 and radiolabeled trastuzumab-$^{111}$In-CHX-A"$^{111}$In-1 was 67.7% and 57.9%, respectively. In the presence of excess unlabeled imaging agent 2 the values were 17.4% for the radiolabeled imaging agent $^{111}$In-2 and 8.4% for the radiolabeled trastuzumab $^{111}$In-1. These values were comparable to those obtained, 13.8% and 7.8%, when excess unmodified trastuzumab was added in the presence of radiolabeled imaging agent $^{111}$In-2 and radiolabeled trastuzumab $^{111}$In-1, respectively.

Example 11

This example demonstrates a synthesis of signaling agent Cy7-Lys(SMCC)-CHX-A" 10 in an embodiment of the invention.

To a solution of amine 9 (3.0 mg, 3.34 µmol) in DMSO (3 mL) was added Cy7 mono-NHS ester (2.50 mg, 3.06 µmol) and Et$_3$N (10 µL). The reaction mixture was stirred under an N$_2$ atmosphere at room temperature for 18 hr and then diluted with Et$_2$O (40 mL). The precipitated product was purified by reverse-phase (RP) semi-preparative HPLC on a C$_{18}$ column using a 0%-50% CH$_3$CN gradient to 15 mM NH$_4$OAc over 30 min followed by lyophilization of the solvent from the relevant fraction to yield trifunctional chelate 10 (1.50 mg, 31%). RP-HPLC: $t_R$=21.5 min; ES-MS m/z: calcd for C$_{78}$H$_{100}$N$_9$O$_{21}$S$_2$ [M−H]$^-$, [M−2H]$^{2-}$: 1562.7, 780.9. Found 1562.4, 780.7.

Example 12

This example demonstrates a conjugation of 10 to cetuximab to form imaging agent 11 in an embodiment of the invention.

Cetuximab

Cetuximab (~10 mg) was reacted with Traut's reagent (Sigma Chemical Co., St. Louis, Mo.) at a 1:15 molar ratio for 1.5 hr at room temperature in 1 mL of PBS plus 10 mM EDTA buffer. Excess Traut's reagent was removed by passage of the reaction solution through a PD-10 column eluted with PBS plus 10 mM EDTA buffer. The number of thiols introduced was determined using Ellman's reagent (Ellman et al., Arch. Biochem. Biophys. 1959, 82, 70-77). Just prior to protein conjugation, 10 was dissolved in the same buffer and then added drop wise to the mAb solution to achieve a molar reaction ratio of 10:1 (10:Cetuximab) and gently vortexed. The solution was then gently agitated in the dark at 25° C. for 1.5 hr. Excess free unreacted SH groups were capped by the addition of iodoacetamide solution (2.0 mM). Finally, the reaction mixture was dialyzed into PBS buffer at 4° C. with 4 buffer changes (4 L total) over 48 hr. Protein concentration was determined by Lowry assay and the number of dye (and chelate) molecules per antibody was calculated based on Cy 7 dye UV absorption at 747 nm. The number of Cy7 dye moieties per cetuximab was calculated to be ~2 based on UV absorption at 747 nm, which then directly corresponds to the same number of CHX-A" chelates on cetuximab according to the 1:1 ratio of Cy7 and CHX-A" within 10.

Example 13

This example demonstrates the radiolabeling synthesis of imaging agent cetuximab-Cy7-CHX-A" (11) in an embodiment of the invention.

A solution of [111]InCl in HCl (0.05 M, 1-3 µL, 0.5-1 mCi) was added to cetuximab-Cy7-CHX-A" (50 µg) contained in $NH_4OAc$ buffer (100 µL, 0.15 M, pH 7), vortexed immediately and incubated at room temperature for 30 min. The reaction was quenched by the addition of EDTA solution (0.1 M, 4 µL). The $^{111}$In labeled antibody was purified by gel filtration chromatography using PD-10 columns (GE Healthcare) eluted with PBS.

Example 14

This example demonstrates cell culture and treatment of trastuzumab-Cy5.5-CHX-A" (2) and cetuximab-Cy7-CHX-A" (11) in an embodiment of the invention.

A431, SKOV3, and NIH3T3 cells were obtained from ATCC (Manassas, Va.). The NIH3T3 cells were transfected with HER2 genes (3T3/HER2+), in order to overexpress HER2 receptors (Di Fiore et al., Science 1987, 237, 178-182). All of the cell lines were grown at 37° C. in the presence of 5% $CO_2$ in DMEM medium supplemented with 1% L-glutamine, and 5% FBS. For the confocal fluorescence microscopy experiments cells were plated in Lab-Tek chambered slides (#178599 Nalge Nunc) at an appropriate dilution and allowed to attach overnight at 37° C. prior to treatment.

To demonstrate the binding of trastuzumab-Cy5.5-CHX-A" (2) and cetuximab-Cy7-CHX-A" (11) by fluorescent microscopy both monoclonal antibodies were used at a concentration of 10 ug/mL in culture medium. The individual cell lines seeded on chambered slides with 60-80% confluency were incubated for 2 hr at 37° C. in the dark. After incubation the cell culture medium was removed and slides were washed three times with PBS (pH=7.4) and immediately fixed in 4% paraformaldehyde prepared in PBS (pH=7.4) for 5 min at room temperature. Fluorescent mounting medium (S3023, DakoCytomation) was added at the time the slide was covered with a cover glass to stabilize the fluorophores before and during confocal microscopy.

For confocal images, cells were examined with a Zeiss LSM 510 confocal system (Carl Zeiss Inc, Thornwood, N.Y., USA) with an Axiovert 100M inverted microscope and operating with a 5 mW HeNe laser tuned to 633 nm. Fluorescence (Cy5.5 or Cy7) and DIC images were collected simultaneously using a 63x Plan-Apochromat 1.4 NA oil immersion objective and a long pass 650 nm emission filter. In the acquisitions for all channels the Zeiss AIM software version 3.2 sp2 (Carl Zeiss GmbH, Heidelberg, Germany) was used. All confocal images were acquired with a frame size of 512 by 512 with identical settings.

The fluorescent labeling of HER2 expressing cells as determined by confocal microscopy studies with trastuzumab- Cy5.5-CHX-A" (2) show excellent binding capability of 2 to genetically engineered cells (NIH3T3-HER2+) which overexpress human HER2 receptors (Di Fiore et al., *Science* 1987, 237, 178-182), indicating that immunoreactivity of the trastuzumab component in 2 is well preserved after modification. In addition, it was shown that 2 strongly binds to intrinsically HER2 over-expressing human SKOV-3 cells as well. When LS174T cells, known to marginally express HER2 receptors in vitro, were incubated with 2, minimal or no binding as observed. Thus, 2 binds HER2-expressing cells and fluorescently labels the cell membrane of both cells genetically engineered to express human HER2 as well as intrinsically HER2 over-expressing SKOV3 cells. This result is comparable to that reported for cell membrane binding of simple fluorescently labeled trastuzumab (Fazekas et al., *Cytometry A*, 2008, 73, 209-219; Gee et al., *Int. J. Cancer* 2007, 121, 2492-2500; Costantini et al., *J. Nucl. Med.* 2007, 48, 1357-1368; Yang et al., *J. Control Release* 2007, 120, 169-177; Tada et al., *Cancer Res.* 2007, 67, 1138-1144; Belimezi et al., *Cancer Immunol. Immunother.* 2006, 55, 1091-1099; and Steffen et al., *Cancer Biother. Radiopharm.* 2005, 20, 239-248). Thus, it has been confirmed that the role of HER2 as a cell surface-specific target and that the functionality of 1 in labeling HER2 over-expressing cancer cells was conserved.

It was observed that cetuximab-Cy7-CHX-A" (11) fluorescence specifically labels EGFR-expressing A431 cells. The fluorescence was mainly membrane associated, but some initial internalization was also visible. In comparison, the cetuximab-Cy7-CHX-A"-labeled A431 cells present the same labeling pattern as seen by others using confocal microscopy with only fluorescent labeled cetuximab (Lin et al., *Cell Mol Immunol.* 2004, 1, 137-141; and Nordberg et al., *Nucl Med Biol.* 2007, 34, 609-618). The experiments confirm full functionality of cetuximab-Cy7-CHX-A" in regard to specific binding and labeling of living EGFR over-expressing cancer cells. Cells that did not express the antigen of interest also did not fluorescently label.

Overall, excellent specificity and functionality for the imaging agents, trastuzumab-Cy5.5-CHX-A" (2) and cetuximab-Cy7-CHX-A" (11), were demonstrated in regard to antigen recognition and binding in cell culture. The specific target binding of the monoclonal antibody in both agents is conserved and they exhibit excellent fluorescence to characterize spatial resolution in confocal microscopy. Accordingly, the conjugated Cy-Dye-CHX-A" component does not interfere with the specificity and binding properties of the antibody.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A signaling agent of formula (I):

wherein
Y' is a chelating moiety that is complexed with a radioisotope;
Z' is a fluorescent dye covalently bonded to L;
X is $C_1$-$C_8$ alkyl, cycloalkyl, cycloalkylalkyl, aryl, or aralkyl; and
L is an α-amino acid residue.

2. The signaling agent of claim 1, wherein X is selected from the group consisting of $C_2$-$C_5$ alkyl, cyclohexyl-$C_1$-$C_4$ alkyl, phenyl, and phenyl-$C_1$-$C_4$ alkyl.

3. The signaling agent of claim 1, wherein the α-amino acid residue is selected from the group consisting of glycine, alanine, valine, and lysine.

4. The signaling agent of claim 1, wherein Y' is selected from the group consisting of CHX-A" (N-[(R)-2-amino-3-(p-aminophenyl)propyl ]-trans-(S,S) -cyclohexane-1,2-diamine-N,N,N',N, "N"-pentaacetic acid), 1B4M (2-(4-aminobenzyl)-6-methyl-diethylenetriaminepentaacetic acid)), 1B4M-DTPA (2-(p-aminobenzyl)-6-methyl-1,4,7-triaminoheptane-N,N',N"-pentaacetic acid), C-DOTA (2-(p-aminobenzyl)-1,4,7,10-tetraazacyclododecane-N,N',N,"N'"-tetraacetic acid), PA-DOTA (1,4,7,10-tetraaza-N-(1-carboxy-3-(4-nitrophenyl)propyl)-N',N",N'"-tris(acetic acid) cyclododecane), and TCMC (2-(p-aminobenzyl)-1,4,7,10-tetraazacyclododecane-N,N'N, "N'"-tetracarboxamide).

5. The signaling agent of claim 1, wherein the radioisotope is selected from the group consisting of $^{213}$Bi, $^{212}$Bi, $^{212}$pb, $^{203}$Pb, $^{225}$Ac, $^{177}$Lu, $^{99m}$Tc, $^{111}$In, $^{124}$I, $^{123}$I, $^{186}$Re, $^{201}$Tl, $^{3}$He, $^{166}$Ho, $^{86}$Y, $^{64}$Cu, $^{89}$Zr, $^{66}$Ga, $^{68}$Ga, and $^{67}$Ga.

6. The signaling agent of claim 5, wherein the radioisotope is selected from the group consisting of $^{64}$Cu, $^{86}$Y, $^{89}$Zr, $^{111}$In, and $^{203}$Pb.

7. The signaling agent of claim 1, wherein the fluorescent dye is selected from the group consisting of an Alexa Fluor dye, a cyanine dye, rhodamine, coumarin, pyrene, dansyl, fluorescein, fluorescein isothiocyanate, carboxyfluorescein diacetate succinimidyl ester, an isomer of fluorescein, R-phycoerythrin, tris(2',2-bipyridyl)dichlororuthenium(II) hexahydrate, Fam, VIC®, NED™, ROX™ (carboxy-X-rhodamine), calcein acetoxymethylester, $DiIC_{12}$, and anthranoyl.

8. The signaling agent of claim 7, wherein the cyanine dye is Cy5.5, Cy5, or Cy7.

9. An imaging agent comprising
(a) a signaling agent of formula (I):

wherein
Y' is a chelating moiety that is complexed with a radioisotope;
Z' is a fluorescent dye covalently bonded to L;
X is $C_1$-$C_8$ alkyl, cycloalkyl, cycloalkylalkyl, aryl, or aralkyl; and
L is an α-amino acid residue; and
(b) a targeting vector conjugated to the reactive maleimide group of the signaling agent.

10. The imaging agent of claim 9, wherein the targeting vector binds to a cell surface antigen associated with a disease.

11. The imaging agent of claim 9, wherein the targeting vector is a peptide, a monoclonal antibody, or a monoclonal antibody fragment.

12. The imaging agent of claim 9, wherein the targeting vector is trastuzumab.

13. A composition comprising (a) at least one signaling agent of claim 1; and (b) a carrier.

14. A composition comprising (a) at least one imaging agent of claim 9; and (b) a carrier.

15. A method of imaging a cancer cell in a mammal comprising
(a) administering to the mammal intravenously the imaging agent of claim 9;
(b) contacting a surface receptor of the cancer cell with the targeting vector of the imaging agent; and
(c) observing a fluorescence emission from the fluorescent dye moiety or detecting an emission from the chelating moiety of the imaging agent by spectroscopy.

16. The method of claim 15, wherein the spectroscopy is single photon emission computed spectroscopy (SPECT) or positron emission tomography (PET).

17. The method of claim 15, wherein the cancer cell overexpresses HER 1 and/or HER2.

18. The method of claim 15, wherein the cancer cell is an epithelial cancer cell.

19. The method of claim 18, wherein the epithelial cancer cell is breast carcinoma, ovarian carcinoma, pancreatic carcinoma, or colorectal carcinoma.

20. A method for obtaining a diagnostic image of a mammal comprising
(a) administering to the mammal the imaging agent of claim 9, in an amount effective to provide an image; and
(b) exposing the mammal to an energy source, whereupon a diagnostic image of the mammal is obtained.

21. The method of claim 20, wherein the diagnostic image is a single photon emission computed spectroscopy (SPECT) image or a positron emission tomography (PET) image.

22. The imaging agent of claim 9, wherein the a-amino acid residue is selected from the group consisting of glycine, alanine, valine, and lysine.

* * * * *